(12) United States Patent
Baumann et al.

(10) Patent No.: US 9,164,114 B2
(45) Date of Patent: Oct. 20, 2015

(54) SUPPLY UNIT FOR CONTINUOUS LOADING

(75) Inventors: Renato Baumann, Steinhausen (CH); Marcel Kaeppeli, Merenschwand (CH); Markus Rinderknecht, Adligenswil (CH); Johann Florian Wassermann, Horgen (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 28 days.

(21) Appl. No.: 13/397,877

(22) Filed: Feb. 16, 2012

(65) Prior Publication Data

US 2012/0269604 A1    Oct. 25, 2012

(30) Foreign Application Priority Data

Apr. 19, 2011   (EP) ................................. 11163035

(51) Int. Cl.
*G01N 21/00*   (2006.01)
*G01N 35/04*   (2006.01)
*G01N 35/00*   (2006.01)

(52) U.S. Cl.
CPC ...... *G01N 35/04* (2013.01); *G01N 2035/00089* (2013.01); *G01N 2035/00306* (2013.01); *G01N 2035/0425* (2013.01); *G01N 2035/0498* (2013.01)

(58) Field of Classification Search
CPC ..................................................... G01N 35/04
See application file for complete search history.

(56) References Cited

U.S. PATENT DOCUMENTS

| | | |
|---|---|---|
| 5,158,895 A | 10/1992 | Ashihara et al. |
| 5,620,898 A | 4/1997 | Yaremko et al. |
| 6,299,840 B1 | 10/2001 | Watanabe et al. |
| 7,360,984 B1 | 4/2008 | Sugiyama et al. |
| 2001/0046437 A1 | 11/2001 | Bramwell et al. |
| 2002/0009391 A1 | 1/2002 | Marquiss et al. |
| 2002/0023444 A1 | 2/2002 | Felder et al. |
| 2003/0197453 A1* | 10/2003 | Jurja ......................... 312/334.46 |
| 2003/0215357 A1 | 11/2003 | Malterer et al. |
| 2004/0037679 A1 | 2/2004 | Sato et al. |
| 2004/0213651 A1 | 10/2004 | Malin |
| 2006/0002820 A1 | 1/2006 | Baumann et al. |
| 2006/0093529 A1 | 5/2006 | Meyer et al. |
| 2006/0105359 A1* | 5/2006 | Favuzzi et al. .................... 435/6 |
| 2010/0028124 A1 | 2/2010 | Lackner et al. |

FOREIGN PATENT DOCUMENTS

| | | |
|---|---|---|
| DE | 100041230 A1 | 3/2002 |
| EP | 0628822 A2 | 12/1994 |
| EP | 0628822 A3 | 12/1994 |
| EP | 1275966 A1 | 1/2003 |
| EP | 1959257 A2 | 8/2008 |
| EP | 1959257 A3 | 8/2008 |
| JP | 200383997 A | 3/2003 |
| WO | 9002326 A1 | 3/1990 |
| WO | 9722882 A1 | 6/1997 |
| WO | 9936787 A1 | 7/1999 |
| WO | 0066269 A1 | 11/2000 |

* cited by examiner

*Primary Examiner* — Jyoti Nagpaul
(74) *Attorney, Agent, or Firm* — David J Chang

(57) ABSTRACT

The present invention relates to a system and method for continuous loading of consumables into an analyzer comprising a stacker unit which can be uncoupled from the transport system for transporting the consumables from the stacker to the analytical modules and within and/or between the analytical modules.

18 Claims, 9 Drawing Sheets

Fig. 6
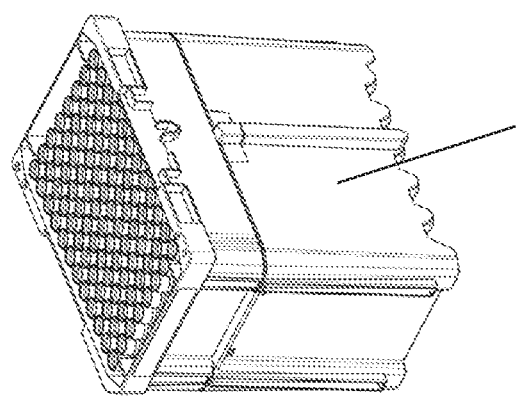
Fig. 6a
60, 70
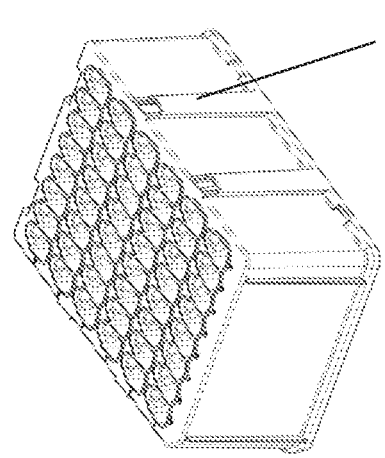
Fig. 6b
101
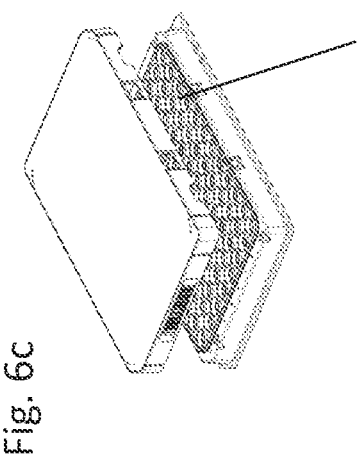
Fig. 6c
301, 302

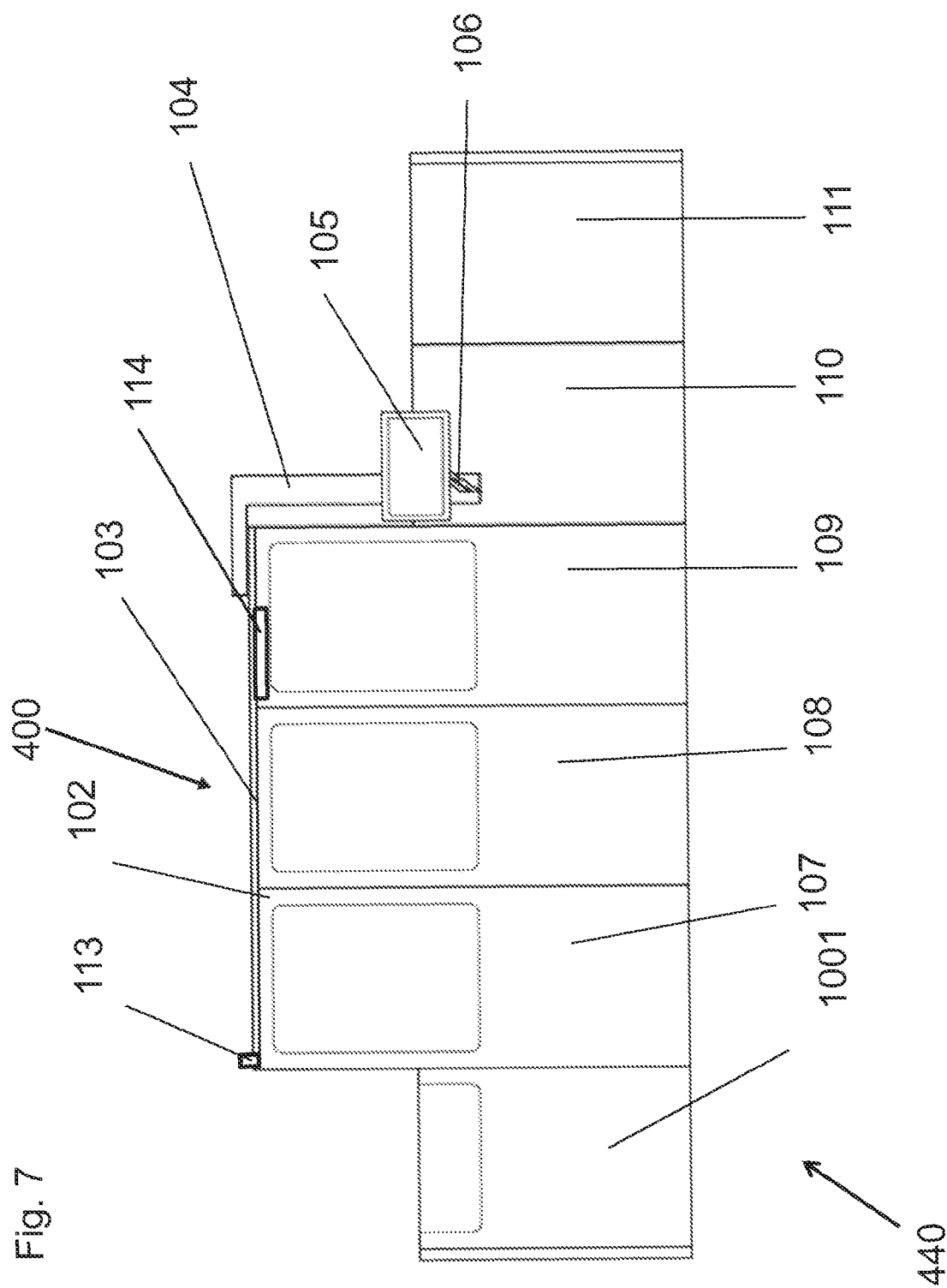

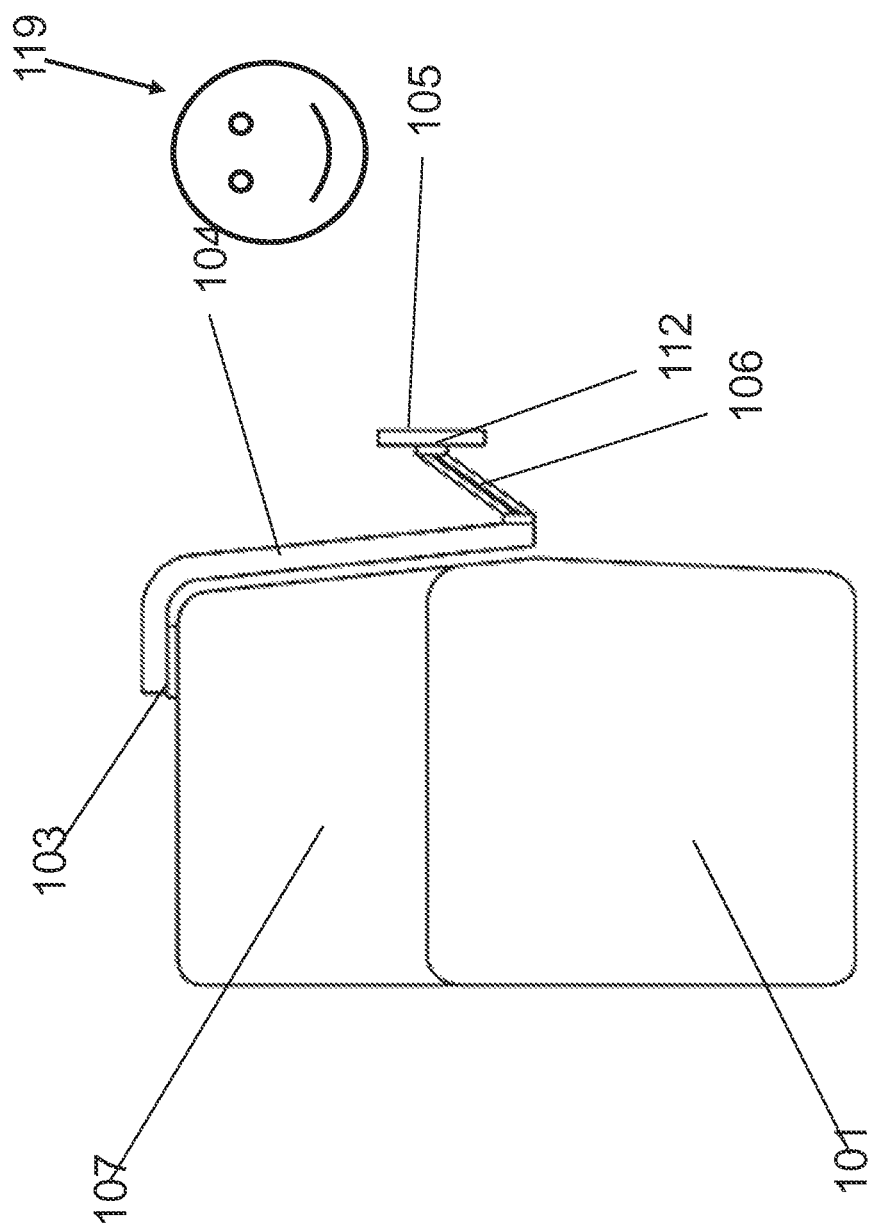

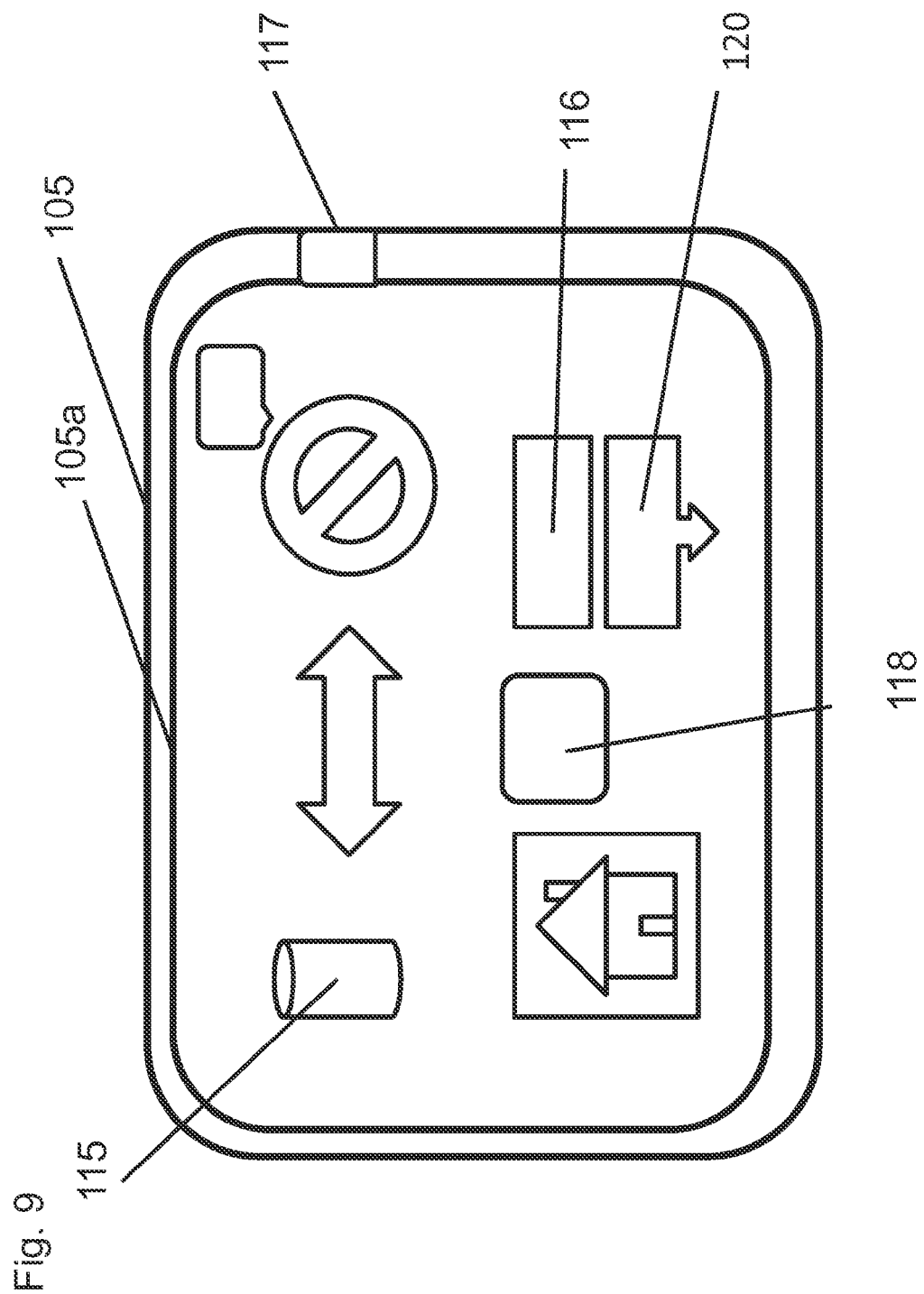

SUPPLY UNIT FOR CONTINUOUS LOADING

CROSS-REFERENCES TO RELATED APPLICATIONS

The present application claims the benefit of priority under 35 U.S.C. §119(a) of EP11163035.6, filed Apr. 19, 2011, the entire contents of which is hereby incorporated by reference.

FIELD OF THE INVENTION

The present invention relates to the field of systems and methods for continuous loading of consumables into analytical apparatuses. Analytical apparatuses commonly require loading of reagents in reagent containers and consumables in order to be able to perform the analytical process.

BACKGROUND OF THE INVENTION

In general, automated analyzers are loaded with consumables necessary to perform an analysis before starting the analysis. In case loading has to be performed during analysis, the analysis has to be interrupted.

EP 1 275 966 discloses a stacker system where a stacker is manually loaded by pulling out a movable platform on which the stacker is mounted and filling the stacker with consumables. Manual loading is only possible when both the supply lifter and the recovery lifter are at their lowest positions. The stacker can, thus, not be loaded while the analyzer is in operation.

The present invention provides an improved system and method for continuously loading consumables into an analytical apparatus.

SUMMARY OF THE INVENTION

The present invention relates to a system for continuous loading of consumables into an analyzer comprising a processing area and a transport system for automatically transporting said consumables within the analyzer. The system comprises a stacker unit comprising at least one stacker for holding consumables. The stacker unit is integrated into the analyzer. The stacker unit is capable of being decoupled from said processing area for manual or automated loading of said consumables. The stacker unit is in a locked position within said analyzer when access to the consumables in the stacker is required by said transport system, and said stacker unit is in an unlocked position for manual loading of consumables when access to the consumables in the stacker is not required by said transport system. The stacker unit has a first end position within the analyzer and a second end position outside of the analyzer. In the second end position, the at least one stackers comprised in the stacker unit are accessible for loading of consumables into the stacker, and the stacker unit is locked during loading.

The invention further comprises a method of continuous loading of consumables into an analyzer, comprising the steps of:
displaying time windows for loading of consumables into a stacker unit on a display;
uncoupling said stacker unit for receiving said consumables from a transport system for transporting consumables from said stacker to said analyzer, and between stations within said analyzer, wherein said stacker unit is integrally mounted within the housing of said analyzer, if a time window for loading of consumables into the stacker unit is available;
sliding said stacker unit to an open position,
locking said stacker unit in said open position,
loading consumables into a consumable holder comprised in said stacker unit while an analytical process is performed within said analyzer,
unlocking said stacker unit when consumables are fully loaded into the stacker unit,
closing said stacker unit, wherein said stacker unit is locked in its closed position to operatively couple to a transport system for transporting consumables.

BRIEF DESCRIPTION OF THE FIGURES

FIG. 6 shows different types of consumables with hardware coding. 6a shows tip racks (60, 70) with hardware coding. 6b shows a deep well multiwell plate (101) with hardware coding. 6c shows a multiwall plate with a lid (301, 302) with hardware coding.

FIG. 7 shows a system comprising an analytical apparatus with a preanalytical module and several analytical modules. A display is attached to a rail which is mounted on top of three of the modules.

FIG. 8 shows a side view of the apparatus with the device attached to a first and a second arm, and a pivot for adjusting the position of the display for optimal user interaction.

FIG. 9 shows a display with a touch screen and different features displayed thereon for user interaction with the analytical system.

DETAILED DESCRIPTION OF THE INVENTION

Figure 1:
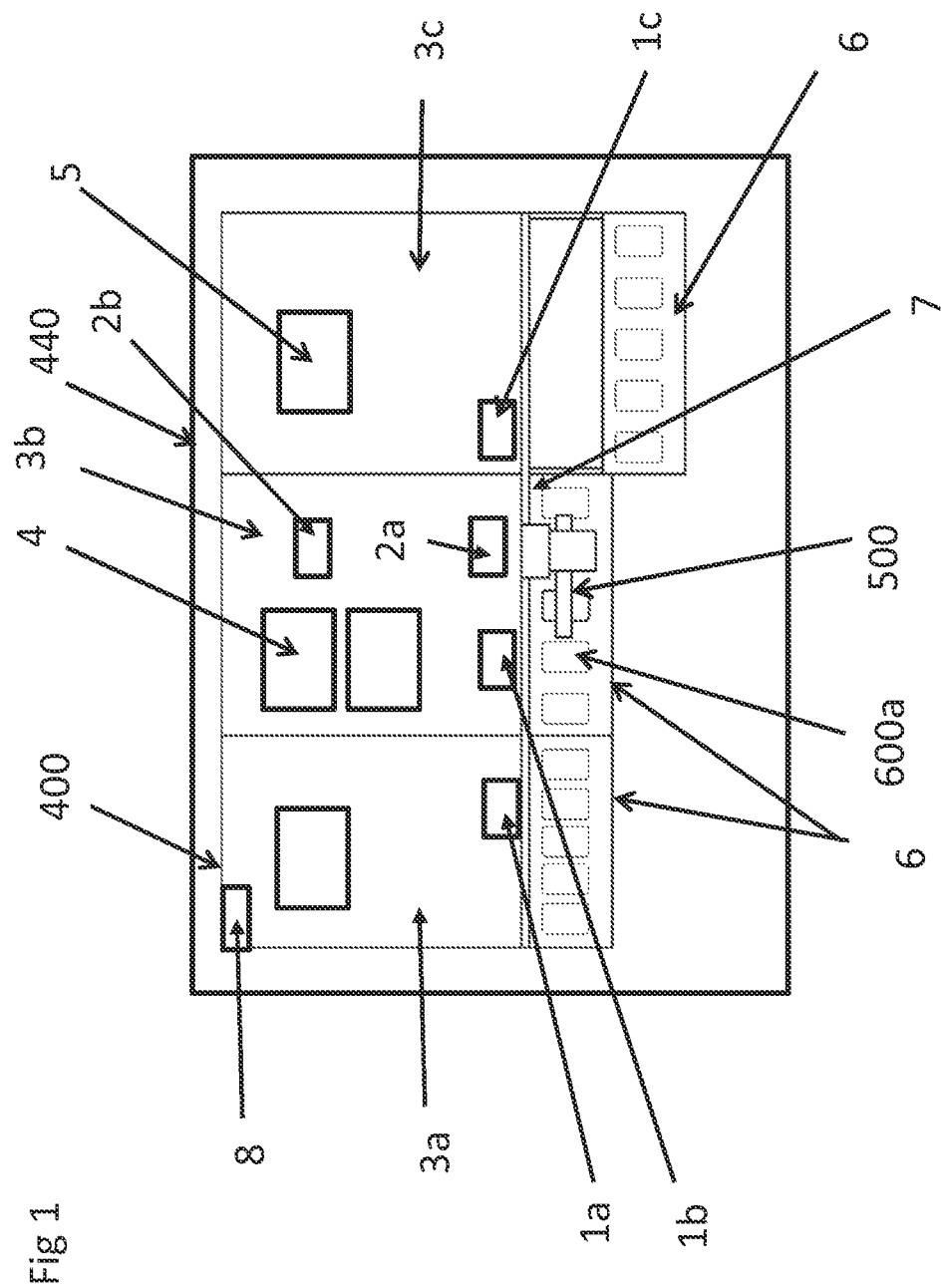
FIG. 1 shows a schematic view of an analytical system with stacker unit drawers.

The present invention provides a system for continuous loading of consumables into an analyzer comprising a processing area and a transport system for automatically transporting said consumables within the analyzer, the system comprising
a stacker unit comprising at least one stacker for holding consumables, wherein said stacker unit is integrated into the analyzer, and wherein said stacker unit is capable of being decoupled from said processing area for manual or automated loading of said consumables, wherein said stacker unit is in a locked position within said analyzer when access to the consumables in the stacker is required by said transport system, and said stacker unit is in an unlocked position for manual loading of consumables when access to the consumables in the stacker is not required by said transport system.

The term "continuous loading" as used herein is understood to mean that the stacker unit of the instrument can be loaded with consumables without interrupting the operation of the analyzer.

The term "consumable" as used herein relates to devices used in the analytical process and subsequently discarded, such as, as non-limiting examples, plastic consumables such as receptacle vessels, multiwell plates, pipette tip holders, etc, and/or reagent containers, or consumables (101,301,302) holding reaction mixes in which the processing or analyzing of the analyte are performed. Embodiments are as described herein.

The term "analyzer" as used herein relates to an apparatus capable of performing an analytical process to detect and/or quantitate at least one analyte.

The term "analyte" as used herein may be any type of biomolecule which is of interest for detection, and the detection thereof is indicative of a diagnostic status of an organism. The organism can be microbial, animal or human. Analytes can be proteins, polypeptides, antibodies or nucleic acids. In one embodiment, the analyte is a nucleic acid.

The term "processing area" as used herein relates to an area within said analyzer where samples to be analyzed are processed for analysis. In one embodiment, said processing area comprises a processing station for pipetting reagents to samples in receptacle vessels. More specifically, said processing station is a separation station or a reaction station. One embodiment of a reaction station is an amplification station.

A "processing station for pipetting reagents to samples" as used herein relates to a station within an analyzer which comprises a pipettor, a holder for holding receptacle vessels and a holder for holding a reagent container.

A "reagent container" is a consumable. In one embodiment, it is made of plastic and holds reagents necessary for performing an analytical process.

A "pipettor" is a device which either couples disposable pipette tips or comprises pipetting needles, and which can aspirate and dispense reagents necessary for performing an analytical process.

A "holder" is a station on which consumables or reagent cassettes are placed, fixed and held in an analytical process.

A "separation station" is understood to be a station where an analyte is separated from a solid support. In one embodiment, the processing area comprises a station for isolating an analyte.

A "receptacle vessel" is a consumable which can hold a sample in an analytical process.

In one embodiment, the processing area comprises a station for reacting said analyte to obtain a detectable signal.

A "reaction station" as used herein is a station in which an analytical reaction occurs. Said analytical reaction is necessary for detecting or measuring an analyte. In one embodiment, said analytical reaction is a reaction producing a measurable signal which correlates with the presence and/or quantity of the analyte in a sample. In one embodiment, the reaction station comprises an incubator for generating a measurable signal. In one embodiment, the reaction station is an amplification station.

The term "transport system" as used herein relates to a system for transporting consumables within said analyzer. In one embodiment, said transport system transports consumables from said stacker unit to at least one processing area within said analyzer, and between processing areas within said analyzer. In one embodiment, said transport system comprises a handler, wherein said handler comprises gripper fingers for gripping said consumables. In one embodiment, said handler is capable of transporting a consumable from said stacker unit to a processing area, and between one processing area and a second processing area.

The term "stacker unit" as used herein relates to a unit which is an integral part of an analyzer and into which consumables are loaded. In one embodiment, the stacker unit comprises more than one stacker for loading consumables. The analyzer may also comprise more than one stacker unit, wherein the stacker units are independent of each other or coupled to each other.

The term "decoupled" as used herein means that the stacker unit is not functionally coupled to the analyzer while being decoupled. When decoupled, the transport system of the analyzer can not access the stacker unit.

The term "in a locked position" is understood to mean that the stacker unit is locked and can not be opened by the operator or user.

The analyzer (400) comprises a computer controller (8) which controls the analytical process. In one embodiment, the computer controller (8) additionally controls a mechanism for unlocking or locking the stacker units (6). When the analytical process requires access to the stacker unit (6) for transferring consumables to the process area (3a,b,c) via the transport system (7), the computer controller (8) locks the stacker unit (6) through the locking mechanism. When no access to the stacker unit (6) is required by the analytical process, the computer controller (8) unlocks the mechanism for locking the stacker unit. Then, the stacker unit is in an "unlocked position". When the mechanism for locking the stacker unit (6) is unlocked, the user or operator can open the stacker unit (6) and load consumables. The opening of the stacker unit and loading of consumables can, thus, occur while the transport system is used for transporting consumables within the analyzer. Thus, it is not necessary to interrupt the analytical process for loading consumables into the at least one stacker of the stacker unit. Rather, the user is only prevented from loading consumables during short time windows when stacker access by the transport system is required. This allows the user to load consumables into the stacker unit while the analytical process(es) are running in the instrument. Thus, in one embodiment of the invention described herein, consumables are loaded into the stacker while the analyte is isolated and/or the analyte is reacting to obtain a detectable signal.

Figure 2:
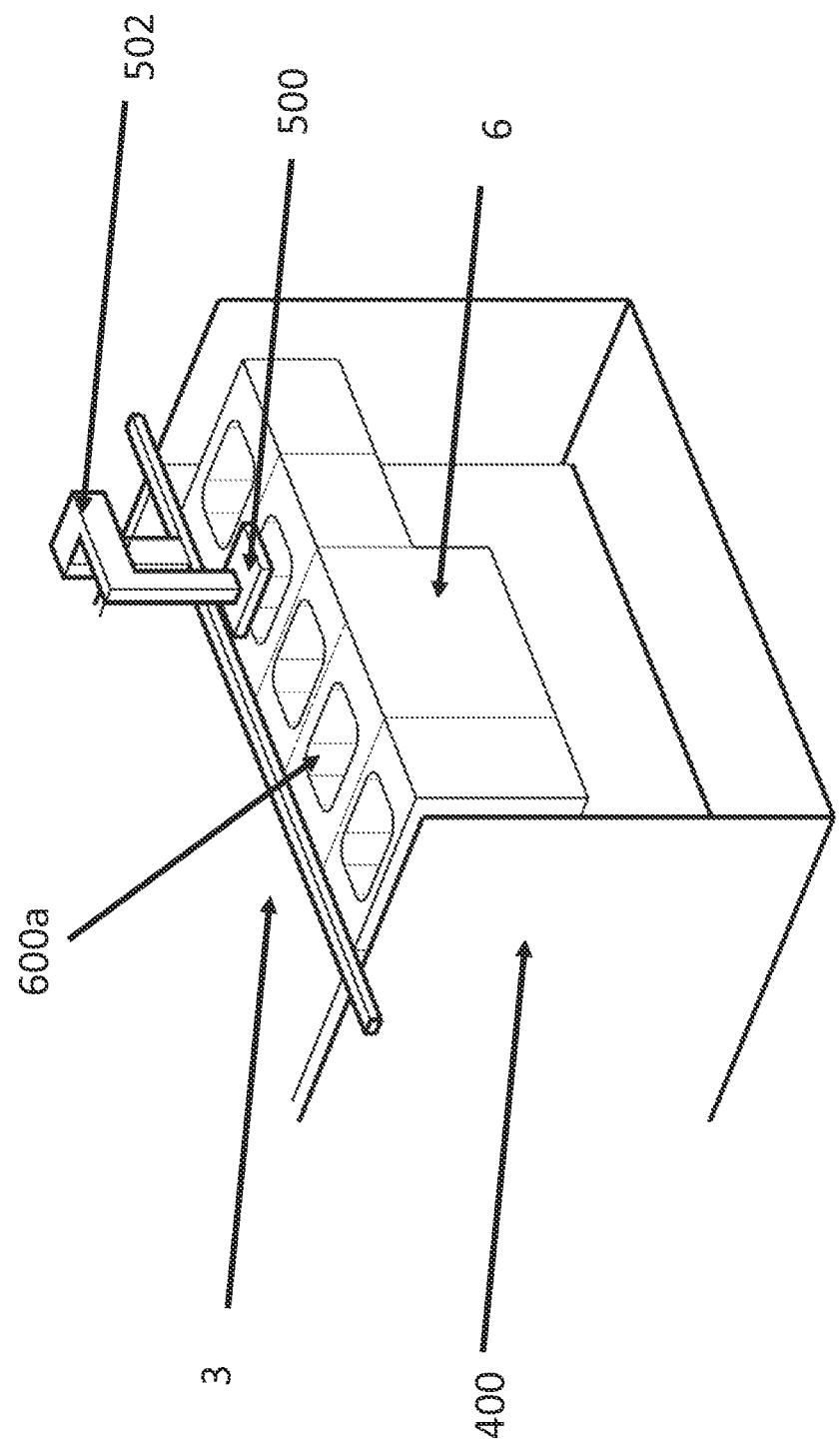
FIG. 2 shows a detail view of a stacker unit with a transport system comprising a handler.
Figure 3:
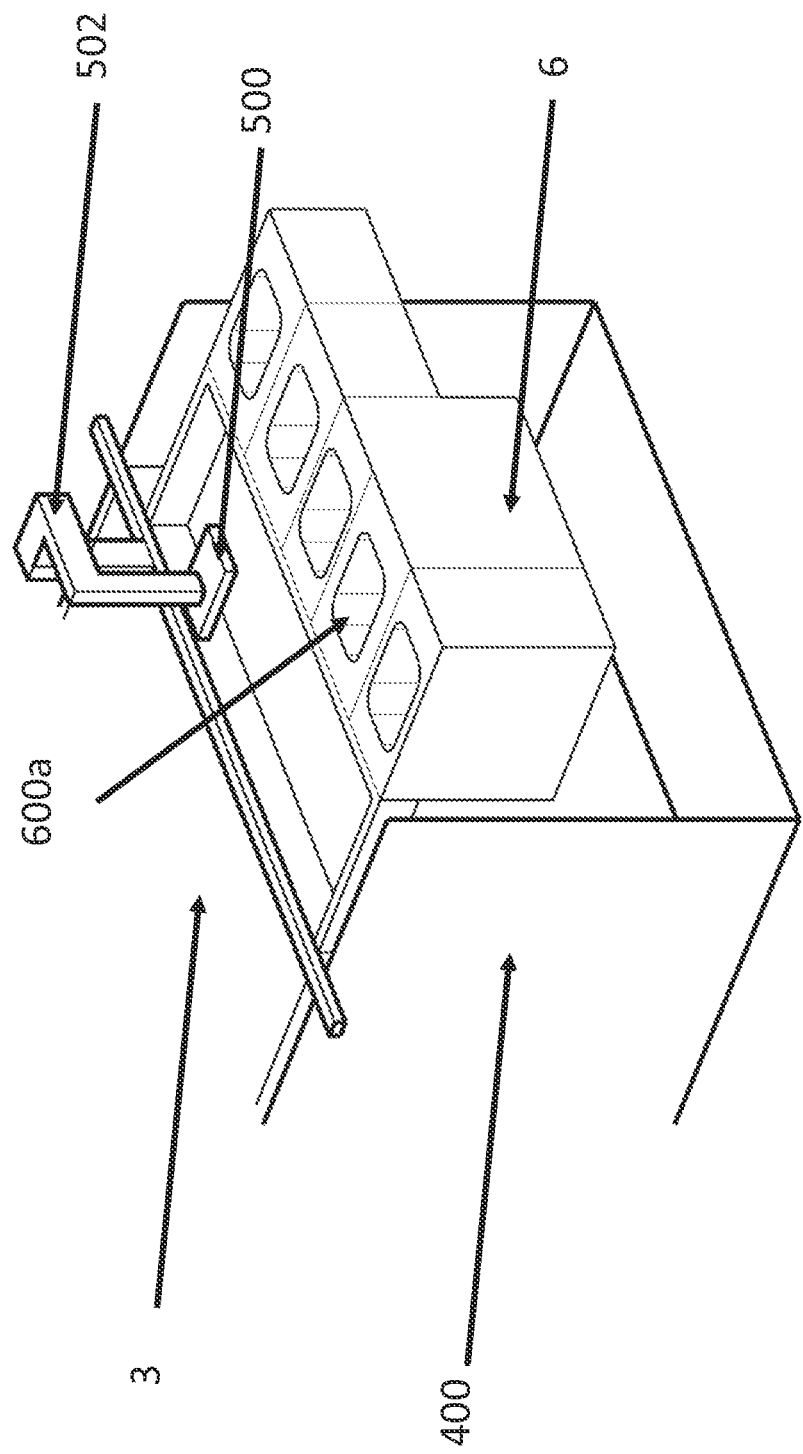
FIG. 3 shows the stacker unit drawer which is open.

The stacker unit has two end positions. A first end position is within the analyzer (see FIG. 2). In this end position, the stackers (600a,b, etc) of the stacker unit (6) are accessible to the transport system (7) for handling of the consumables stacked in the stackers (600a,b). A second end position is outside of the analyzer (see FIG. 3). In this second end position, the stackers (600) of the stacker unit (6) are accessible for loading of consumables into the stacker, either automatically or manually. In one embodiment, at least one end position, more specifically both end positions can be locked. Thus, there may be an inside lock and/or an outside lock. The advantage of the inside lock is that it ensures that the handler can access the consumables in the stackers, and that the process is not interrupted or the analyzer damaged mechanically by sudden opening of the stacker unit. The outside lock ensures that mechanical damage to the stacker and analyzer is avoided by complete and correct loading of consumables into the stackers.

In one embodiment, the stacker unit has a first end position within the analyzer and a second end position outside of the analyzer. In the second end position, the at least one stackers comprised in the stacker unit are accessible for loading of consumables into the stacker, and the stacker unit is locked during loading.

The advantage of locking the stacker unit in the second end position is that the user can not close the stacker unit before the consumables are properly and completely loaded. The locking in the second end position, thus, prevents damage to consumables which would occur if the stacker units were closed before the consumables are completely loaded.

An analytical system is also disclosed, which comprises an automated mechanism for automatically sliding a drawer which functionally couples to the analytical process when in a first end position inside the analyzer and when locked in said position, into the first end position within the analyzer before locking the stacker unit in its locked position, inside the analyzer. In one embodiment, the drawer is the stacker unit disclosed herein. In another embodiment, the drawer comprises a waste container which, when loaded into the analyzer and locked, interfaces with an outlet from the analyzer through which waste is discharged into the waste container. The automated mechanism may only be active for a partially open stacker unit. In such an embodiment, the stacker unit would be manually closed partially until a position is reached where the automated sliding mechanism becomes active. For example, the automated closing mechanism may be active only for the last 1 to 10 cm before reaching the first end position, or 1 to 5 cm or 2 to 5 cm. In one embodiment, the opening and closing of the stacker unit is completely automated. In such an embodiment, the automated closing mechanism is active between the second end position and the first end position of the stacker unit. The advantage of the automated closing mechanism is that the drawer will always be placed exactly in its first end position within the analyzer, without possibility of canting or twisting within the analyzer. Canting or twisting of the stacker unit within the analyzer could lead to malfunctions of the drawer during the analytical process or could lead to damage to the instrument. The automated closing mechanism prevents such malfunctions and/or damages. Automated mechanisms for sliding a drawer into a first end position are well known to the skilled person.

Figure 4:
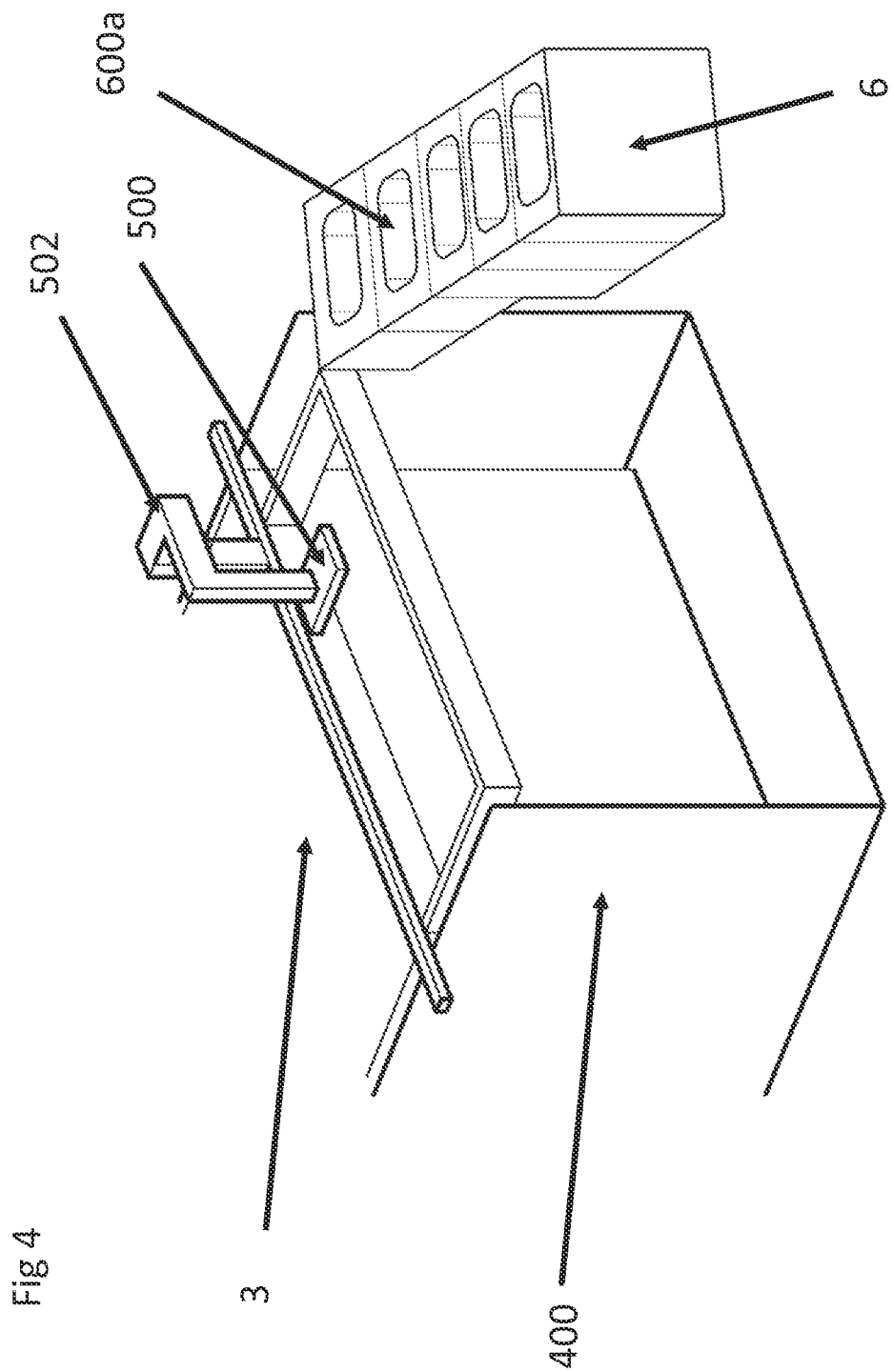
FIG. 4 shows the pivotable stacker unit drawer which is turned sideways.

In one embodiment, the stacker unit is mounted in front of the transport system. This allows easy access for the user. One embodiment of the stacker unit is a drawer. Decoupling comprises opening of the drawer for loading of consumables when the stacker unit is unlocked. One embodiment of a stacker is a pivotable unit, specifically, a pivotable drawer (see FIG. 4). This provides easy access to the stacker for service or repair.

The analyzer may comprise additional identification mechanisms for helping the user to load and unload the consumables from the analyzer. Such mechanisms include, as non-limiting examples, light barriers or bar codes or RFID. In one embodiment, loading and unloading locations are always on the top end of the stackers.

The stackers may either be loaded manually or automatically. Loading with consumables may be effected from the top. In one embodiment, any one stacker is constructed and arranged to receive a specific consumable.

In one embodiment of the system herein described, the consumables are hardware-coded.

The analytical system (440) further comprises more than one type of consumables (60, 70, 101,301,302), wherein said consumables (60, 70, 101,301,302) have essentially a same footprint, and wherein any type of consumables (60, 70, 101, 301,302) comprises a unique surface geometry (601). Furthermore, the system also comprises a system comprising specific recognition elements for distinguishing said different consumables wherein any one of said recognition elements comprises a unique surface geometry complementary to a unique surface geometry of a specific type of consumable. In one embodiment, said system for distinguishing said different consumables (60, 70, 101,301,302) constructed and arranged to recognize specifically said unique surface geometry (601).

Consumables (60, 70,) with essentially identical footprint are plastic consumables for storing other consumables, such a pipette tips or single tubes, of for holding reagents and samples, or consumables (101,301,302) holding reaction mixes in which the processing or analyzing of the analyte are performed. Specific embodiments of such consumables are racks (60, 70) or multiwell plates (101,301,302). Different types of multiwell plates (101,301,302) with identical footprint can be used in the system (440). Such types of multiwell plates (101,301,302) are multiwell plates for storing samples or reagents, multiwell plates for isolating and analyzing an analyte, and/or multiwell plates for reacting an analyte to obtain a detectable signal. In a specific embodiment, if the analyte is a nucleic acid, the reacting may be any type of amplification of nucleic acids known to the person skilled in the art. In one embodiment, said consumables (60, 70, 101, 301,302) comprise at least one tip rack (60, 70) and one multiwell plate (101, 301). In one embodiment, said footprint comprises a length and width of the base corresponding to ANSI SBS footprint format. In one embodiment, the length is 127.76 mm +/−0.25 mm, and the width is 85.48 mm +/−0.25 mm.

The term "surface geometry" relates to the surface structure, more specifically the surface structure of the side walls of the consumables (60, 70, 101,301,302). The surface geometry comprises hardware identifiers, more specifically recesses and/or ridges integrally formed in the surface of a consumable (60, 70, 101,301,302). In one embodiment, any one of all types of consumables (60, 70, 101,301,302) with said footprint comprise a unique surface geometry (601). A "unique surface geometry" is understood to be a surface geometry (601) as hereinbefore described which is unique for a type of consumable (60, 70, 101,301,302) and is substantially different from the surface geometries (601) of other consumables (60, 70, 101,301,302) such that the consumable (60, 70, 101,301,302) is specifically recognized by the recognition system of the analytical system (440).

In a specific embodiment, the system comprises stackers (600a,b) for stacking multiple consumables (60, 70, 101,301, 302) of one type, wherein any one of said stackers (600a,b) comprises recognition elements for one type of consumable (60, 70, 101,301,302). The term "stacker" as used herein relates to the uptake area in the analytical system for a specific consumable (60, 70, 101,301,302). The multiple consumables (60, 70, 101,301,302) of a specific type are stacked in the stacker (600a,b). Individual consumables (60, 70, 101, 301,302) of one type are then retrieved from the stacker (600a,b) within the system (440) and automatically transported to the processing area (3a, 3b, 3c) in which they are used, either by a conveyor or, in one embodiment, by a handler (500) connected to a robotic arm (502). Thus, due to the unique surface geometry (601) of the consumable (60, 70, 101,301,302), a specific type of consumable (60, 70, 101,301, 302) can only be loaded into a specific stacker (600a,b). This prevents the user from loading the wrong consumable (60, 70, 101,301,302) into a specific stacker (600a,b), even if the consumables (60, 70, 101,301,302) have the same footprint.

In a specific embodiment, more than two different types of consumables (60, 70, 101,301,302) with a same footprint are comprised in the system (440). In a more specific embodiment, more than three different types of consumables (60, 70, 101,301,302) with a same footprint are comprised in the system (440). The consumables (60, 70, 101,301,302) are more specifically selected from the group consisting of tip rack (60, 70), multiwell plate (101) for sample preparation, multiwell plate (302) for amplification and/or detection, reagent cassette holder, tube holder etc.

A method is also provided for recognizing the identity of a consumable (60, 70, 101,301,302) within an analyzer (400) as described hereinbefore. Said method comprises providing one type of consumable (60, 70, 101,301,302), wherein said one type of consumable (60, 70, 101,301,302) comprises a unique surface geometry (601). The method further comprises interacting said one type of consumable (60, 70, 101, 301,302) comprising a unique surface geometry (601) with a stacker (600a,b) comprising recognition elements (602) specific for said unique surface geometry (601). The consumable (60, 70, 101,301,302) is then identified when the unique surface geometry (601) is engaged by the recognition elements (602). The term "recognition elements" as used herein relates to elements, such as a guidance (602) mounted on the inside of a stacker (600a,b) which fits specifically with the unique surface geometry (601) of one type of consumable (60, 70, 101,301,302). Embodiments analyzer (400), consumable (60, 70, 101,301,302) and stacker (600a,b) are as defined herein.

Finally, a consumable (60, 70, 101,301,302) is also provided comprising a unique surface geometry (601) constructed and arranged to allow a stacker (600a,b) to specifically identify the type of consumable (60, 70, 101,301,302). Embodiments of consumable (60, 70, 101,301,302), stacker (600a,b) and surface geometry (601) are as herein described. Exemplary consumables are shown in FIG. 6.

Figure 5:
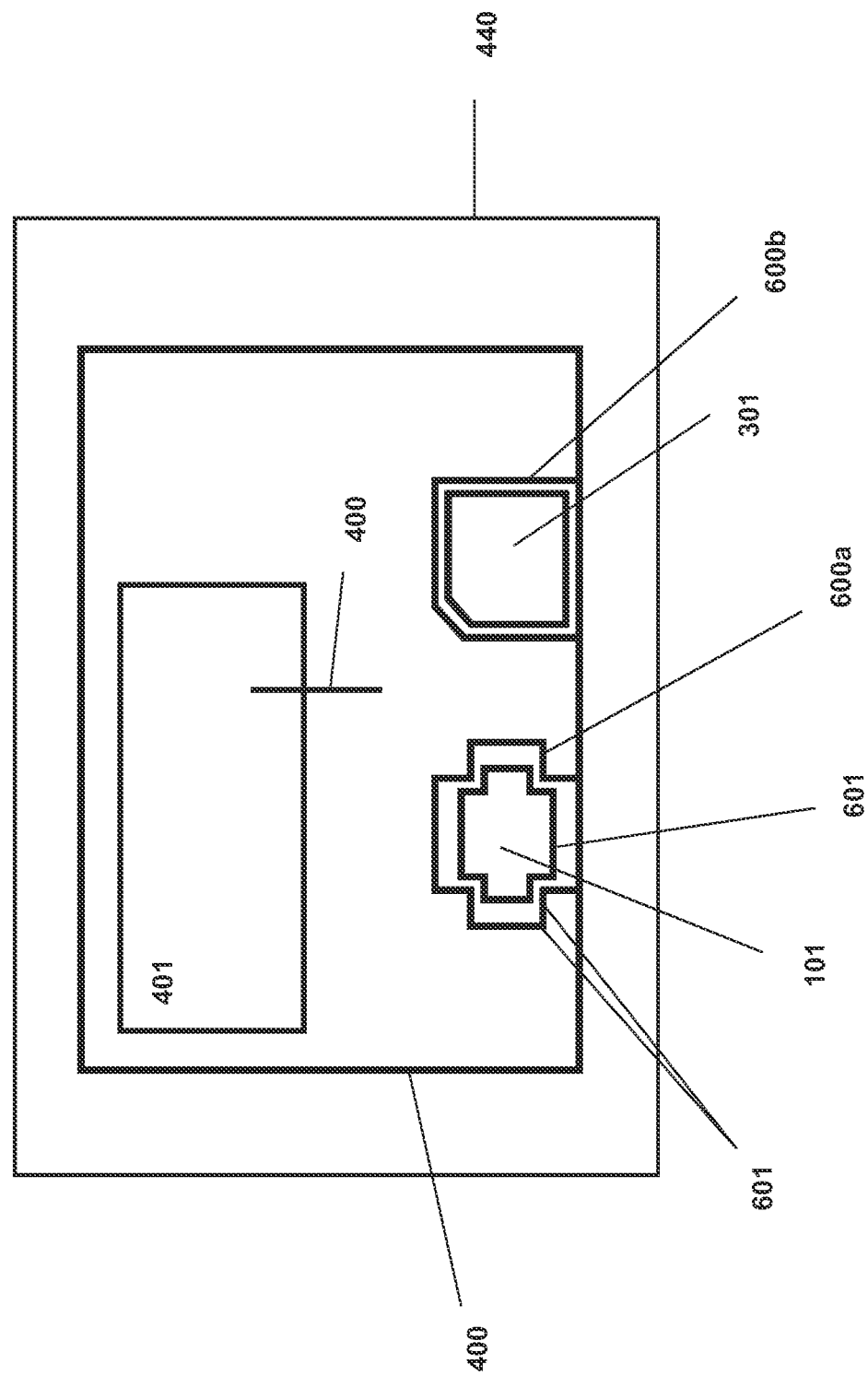
FIG. 5 shows a system with hardware coding of consumables and corresponding stackers.

A schematic drawing of an exemplary analytical system (440) is shown in FIG. 5. The recognition of the surface geometry (601) by the stacker (600a,b) is shown in FIG. 5. The inner surface of the stacker (600a,b) comprises recognition elements (602). It is constructed and arranged to engage the surface geometry (601) of the consumable (60, 70, 101, 301,302) and, thereby, the type of consumable (60, 70, 101, 301,302) is specifically recognized and loading of the wrong type of consumable (60, 70, 101,301,302) is avoided. In a specific embodiment, more than one type of multiwell plate is used in the analytical system (440), more specifically in different steps of the analytical method. Thus, different types of multiwell plates (101,301,302) have different surface geometries that are unique for each type of multiwell plate (101, 301,302). Each type of multiwell plate (101,301,302) is specifically recognized by its unique surface geometry (601).

In specific embodiments of the present invention, the analyzer (400) comprises a housing (102), and the stacker unit (6) is integrated into the housing (102) of the analyzer (400). The stacker unit (6) comprises more than one single stackers (600) or stacker modules (600). Each of said stackers (600a,b) is capable of specifically recognizing a specific consumable through hardware coding as described herein.

In one embodiment of the present invention, access to the stacker unit (6) for loading and/or unloading is guided via display (105).

The present invention also provides a method of continuous loading of consumables into an analyzer, comprising the steps of:
  uncoupling said stacker unit for receiving said consumables from a transport system for transporting consumables from said stacker to said analyzer, and between stations within said analyzer, wherein said stacker unit is integrally mounted within the housing of said analyzer, if a time window for loading of consumables into the stacker unit is available;
  sliding said stacker unit to an open position,
  locking said stacker unit in said open position,
  loading consumables into a consumable holder comprised in said stacker unit while an analytical process is performed within said analyzer,
  unlocking said stacker unit when consumables are fully loaded into the stacker unit,
  closing said stacker unit, wherein said stacker unit is locked in its closed position to operatively couple to a transport system for transporting consumables.

The advantages of the method are as described herein for the system for continuous loading.

In one embodiment, the analytical process comprises handling of consumables between stations within said analyzer by said transport system. Thus, the transport system transports consumables from the stacker unit to stations within the analyzer where the consumables are used in the analytical process, and additionally also transports consumables during the analytical process between stations within the analyzer. In one embodiment, the consumables from the stacker are transported to an intermediate station by a first handler of the transport system. A second handler of the transport system then transports the consumable to a station where the consumable is used in the analytical process. In one exemplary embodiment, the consumable is a multiwell plate and the transport system transports the multiwell plate from the stacker to an intermediate station, and from the intermediate station to a station for pipetting samples into the wells of the multiwell plate. The multiwell plate with the added samples is then transported by the transport system to a separation station where isolation of the analyte comprised in the samples is performed. The transport system, furthermore, transports a second multiwell plate comprising the isolated analytes to a reaction station, which, in one embodiment is an amplification station for amplification of nucleic acids.

In one embodiment of the method disclosed herein, time windows (120) for loading of consumables into a stacker unit are displayed on a display (105).

In one embodiment, the transport system comprises one or more handlers, more specifically two or more handlers for transporting consumables within the analytical apparatus. The transport system is, in one embodiment, integrally mounted within said analyzer. The analyzer further comprises a housing. In one embodiment, the stacker units are integrated into the housing of the analyzer. This ensures that the stacker and stacker handler is covered by the housing and is shielded from the user.

In one embodiment, the stacker unit is a drawer. The uncoupling comprises opening of said drawer and locking said drawer in an open position. In this position, the transport system can still transport consumables between stations within the analyzer. Thus, uncoupling of the stacker unit does not interrupt the analytical process. Interruption of the analytical process is prevented by only permitting the uncoupling of the stacker unit when the analytical process does not require transporting consumables from the stacker unit to stations within the analyzer. The integration of the transport system into the housing of the analyzer and the drawer shape of the stacker units have the advantage that the stackers are ergonomic and user-friendly. The analyzer thereby has a reduced footprint. The integration of the transport system and the stacker units into the housing also prevents contamination of the consumables.

In one embodiment, the analyzer may comprise at least two stacker units which can be independently uncoupled from the analyzer for loading of consumables. In this embodiment, the at least two stacker units comprise stackers for the same types of consumables. The transport system can choose between the stacker units when transferring consumables from the stacker units to stations within the analyzer.

The present invention, thus, provides extended time windows for the user for loading and unloading consumables during the analytical process with minimal downtime for the analyzer. Walk away time and flexibility are optimized. This also provides for cost savings for the user. The use of hardware coding as described herein and of display assisted loading also prevent errors when loading consumables, and damage to the analyzer.

A method for functionally coupling a drawer as described herein of an automated analytical apparatus with the analytical process is also disclosed which comprises automatically sliding the drawer into first end position within the analyzer as described herein and locking the drawer, thereby functionally coupling the drawer to the automated analytical apparatus. In one embodiment, the drawer is partially closed manually, and is the fully closed automatically. In another embodiment, the drawer is closed completely automatically.

User Interaction with Automated Analytical Apparatus

The present disclosure relates to a method of interaction between an automated analytical apparatus for performing an analytical process in at least one analytical module, and a user, said method comprising displaying all features necessary for performing said analytical process on a display, wherein said display is mounted in front of said automated analytical apparatus. The mount of said display is constructed and arranged to move the display laterally along at least one of said modules. Moving the display into a position overlapping with a module, prevents access to the module. Moving the display into a position not overlapping with a module enables access to the module.

This has the advantage that all user interaction relating to performing the analytical process can be guided entirely by the display. A further advantage is that the display, which is mounted in front of the analytical apparatus and can be moved laterally along at least part of said apparatus can be brought into a position close to the module which needs to be accessed by the user without interfering with access. Accessing may e.g. opening of a stacker and loading of consumables, or loading of reagent containers into the apparatus. As the display is mounted such that it is positioned in front of the apparatus, access of the module in front of which the display is located cannot be accessed from the front. Positioning of the display in a non overlapping position can be achieved as described herein. During moving and in any position in front of the apparatus, the display always displays all features necessary for performing the analytical process. The display may also be moved sideways in one end position to enable access to a module.

In one embodiment, the analytical apparatus comprises a module for loading sample vials onto the analytical apparatus. This module is considered a pre-analytical module, and the process of loading sample vials into the analyzer is considered a pre-analytical process, as opposed to an analytical process, which relates to processes such as liquid transfer, transfer of receptacles in which processing of a sample occurs, reactions etc. The interaction between any pre-analytical module and the analytical apparatus may be performed via the display, or such interaction may be autonomous. Thus, "all features necessary for performing an analytical process" relates to the analytical processes herein described, not to pre-analytical processes. However, the features necessary for performing the analytical process also comprise processes such as loading of reagents and consumables which are required to perform the analytical process.

The term "module" as used herein relates to any spatially defined location within the analyzer. Two modules (e.g. 108, 109) can be separated by walls, or can be in open relationship. Any module (107, 108, 109, 110, 111) can be either autonomously controlled, or control of the module (107, 108, 109, 110, 111) can be shared with other modules (107, 108, 109, 110, 111). In one embodiment, all modules (107, 108, 109, 110, 111) are controlled centrally. Transfer between modules (107, 108, 109, 110, 111) can be manual or automated.

The term "in front of said automated analytical apparatus" is meant to refer to the side of the analytical apparatus where the user interaction during operation of the analytical apparatus occurs. Interaction with the analytical apparatus for maintenance or repair when the analytical apparatus is not in operation may also occur on other sides than the front of the automated analytical apparatus.

Displays are well known in the art. In one embodiment, the display (105) comprises a touchscreen (105*a*).

One analytical process comprises reacting an analyte with a compound. The term "reacting" as used herein relates to any type of chemical reaction of the analyte with reagents that is necessary to obtain a detectable signal. In one embodiment, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

Another analytical process comprises isolating and separating an analyte from other material.

In one embodiment of said method herein described, the mount of said display is constructed and arranged to move the display laterally along at least one of said modules. In one embodiment, the display (105) is mounted on a rail (103) which extends along the front of the top side of at least one module (107,108,109), see FIGS. 1 and 2. The display (105) can be moved along the rail (103), resulting in a horizontal movement of the display (105) along the at least one module (107,108,109,110,111). In one embodiment, the rail (103) extends along at least two modules (107,108).

In one embodiment of the method herein described, the method comprises accessing a module (e.g. 107), wherein said display is moved to a position not overlapping with said module (107). In one embodiment, when the rail (103) extends along at least two modules (e.g. 107 and 108), the display is moved to a second module (108) in order to access the first module (107).

Specifically, features (115) displayed by said display comprise the loading status (115) of the apparatus (400), and/or the loaded consumable amount, and/or information on when the modules are accessible for loading or unloading of consumables and/or reagents (116). An exemplary display (105) with features (115) is shown in FIG. 9.

The advantage of displaying all features necessary for performing the analytical process is that the user can control the analytical process entirely from the display. Although the apparatus may additionally comprise optional lights or indicators for easier and quicker identification of the part of the apparatus requiring action, the display allows controlling all modules required for performing the analytical process in the analytical apparatus from the display. Thus, the user does not need to check controls in different locations of the apparatus before performing an action. This makes it easier for the user to safely operate the analytical apparatus.

Specific actions controlled by said display comprise unlocking a drawer by requesting drawer unlock via the display (105). A drawer is, in one embodiment, a drawer comprising a stacker unit (6) for loading and stacking consumables. A user interface (116) on the display (105) to display loading step guidance of stacker units (6) may also be included (see FIG. 9). One stacker unit may comprise at least one stacker (600). Further specific actions are: automatic opening of housing (102), wherein a request for opening and action to open the housing (102) are entered and controlled via the display (105). In one embodiment, a button (117) on the side of the display (105) is present (see FIG. 9), wherein said button (117) has to be engaged simultaneously with a button (118) on the touchscreen of the display (105). This requires the user (119) to use both hands, thus reducing the risk of opening the lid accidentally, and prevents the user from being close to the automated door.

According to the method of the present disclosure, control and operation of at least the analytical part of the apparatus are fully managed via said display. In one embodiment, additional control devices are absent. In another embodiment, supplementary optional control lights and/or light barriers are present on selected parts.

Further specific features displayed by the display comprise walk-away time until reload of the apparatus, and/or displaying next required user action by showing differently colored time windows for different user action on said display. In one embodiment, the analytical process is not stopped during reloading of the apparatus. The timing of the reload is, thus, defined solely by the requirement for new consumables or reagents, but not by the status of the analytical process.

Further features can be comprised on said display which are either required for controlling the function of the automated analytical apparatus or provide the user with information which allows optimization of walk-away time.

The present disclosure also relates to a fully automated analytical apparatus (400) comprising at least one module (107,108,109) for performing an analytical process, a control unit (114) and a display (105), wherein said display (105) is mounted in front of said analytical apparatus (400) and wherein said mount of said display (105) is constructed and arranged to move the display (105) laterally along at least one module (107,108,109) of said apparatus (400). When the position of the display (105) overlaps with a module (107, 108,109), access to the module (107,108,109) is prohibited and when the display (105) is located in a non-overlapping position of said module (107,108,109), access to said module (107,108,109) is enabled. All features (115) necessary for performing said analytical process are displayed on said display (105).

In one embodiment, the mount of the display (105) is coupled to at least one guiding rail (103) or rails (103) on at least one module of said apparatus (400). In one embodiment the mount (104) of the display (105) is coupled to a double rail (103).

In one embodiment, the mount of said display may be coupled to an upper track for guidance, specifically, a cable conduit, and a lower track.

In one embodiment, the upper track or rail (103) comprises an arrestor (113) at least at one end of the at least one module. This arrestor (113) allows the display to be arrested in the end position. In one embodiment, the display mount is rotatable to the side of the modules. This allows rotation of the display to the side to not block doors that need to be accessed.

In one embodiment of the mount of the display, the mount comprises a first arm (104), wherein said first arm (104) is connected to the rail (103), and a second arm (106), wherein said second arm (106) is connected to said first arm (104), comprises a pivot (112) to which the display (105) is connected. The pivot (112) permits lateral adjustment of the display (105). The connection between pivot (112) and display (105) is constructed and arranged to allow vertical/incline adjustment of the display (105). This has the advantage that the display (105) can be adjusted vertically for optimal reach by the user (119), and for providing free access to the bottom level for loading and unloading.

In one embodiment, the analytical apparatus may comprise additional pre-analytical modules (1001). Pre-analytical modules are modules which do not participate in the analytical process. Such pre-analytical modules may be modules which sort sample tubes, provide sample tubes comprising samples to be analyzed to the analytical modules. The rail (103), in this embodiment, may run along all modules (1001, 107, 108, 109, 110, 111), or it runs only along the top of modules (107, 108, 109, 110, 111) or only along one or more modules comprising a separation station (107,108,109). A "separation station" is understood to be a station where an analyte is separated from a solid support. In one embodiment, the processing area comprises a station for isolating an analyte.

The display (105) may be provided with or without a keyboard. In one embodiment, the display (105) is non-detachable.

In one embodiment, the apparatus unit recognizes which drawer is open and the control unit (114) of the apparatus controls the automatic movement of the display (105) to a position where action is required. This has the advantage that the user does not need to first go to the display (105) and move it to an appropriate position to carry out a task, but can immediately go to the display (105) and take care of the required action. The display (105) may also recognize its position along the system (440) and display (105) context and/or position related information. The display (105) may also automatically recognize where an action is required and automatically move to the respective position.

The invention claimed is:

1. A system for continuous loading of consumables into an analyzer wherein said analyzer comprises:
   at least one separation station for isolating nucleic acids;
   at least one amplification station for amplifying nucleic acids;
   a transport system for automatically transporting said consumables within the analyzer, wherein said transport system comprises a first handler and a second handler, wherein said first handler and said second handler comprise gripper fingers for gripping said consumables;
   a stacker unit comprising at least one stacker for holding consumables, wherein said stacker unit is integrated into the analyzer, and wherein said stacker unit is capable of being decoupled from said analyzer for manual or automated loading of said consumables, wherein said stacker unit is in a locked position within said analyzer when access to the consumables in the at least one stacker is required by said first handler for transporting consumables from said stacker unit to an intermediate station, and said stacker unit is in an unlocked position when access to the consumables in the stacker is not required by said first handler, wherein at said unlocked position, opening of said stacker unit and loading of consumables can occur while said second handler is used for transporting consumables between said intermediate station and said at least one separation station or while said first handler is used for transporting consumables to said at least one amplification station; wherein the stacker unit has a first end position within the analyzer and a second end position outside of the analyzer, and wherein, in the second end position, the at least one stacker comprised in the stacker unit is accessible for loading of consumables into the stacker, and the stacker unit is locked when in the second end position;

and a computer controller that controls a mechanism for unlocking said stacker unit and for locking said stacker unit in the first end position or in the second end position.

2. The system according to claim 1, wherein said system comprises an automated mechanism for automatically sliding the open stacker unit into the first end position within the analyzer before locking the stacker unit in its locked position inside the analyzer.

3. The system according to claim 1, wherein the stacker unit is a drawer, and said decoupling comprises opening of the drawer for loading of consumables when the stacker unit is unlocked.

4. The system according to claim 1, wherein the opening and closing of the stacker unit is completely automated.

5. The system according to claim 1, further comprising more than two different types of consumables, wherein any one stacker is constructed and arranged to receive one specific type of consumables.

6. The system according to claim 5, wherein each one type of said more than two different types of consumables comprises a unique surface geometry.

7. The system according to claim 1, wherein said stacker unit is a pivotable unit.

8. The system according to claim 1, wherein said consumables are hardware-coded.

9. The system according to claim 1, wherein access to the stacker unit for loading and/or unloading consumables is guided via a display.

10. The system according to claim 1, wherein said consumables are loaded into the stacker while nucleic acids are isolated in the at least one separation station and/or nucleic acids are amplified in the at least one amplification station.

11. A method of continuous loading of consumables into an analyzer, comprising the steps of:
    uncoupling a stacker unit comprising at least one stacker for receiving said consumables from a transport system comprising a first and a second handler wherein said first handler comprises gripper fingers for gripping said consumables and transports said consumables from said at least one stacker to an intermediate station within said analyzer, wherein said stacker unit is integrally mounted within the housing of said analyzer,
    sliding said stacker unit to an open position,
    locking said stacker unit in said open position,
    loading consumables into said at least one stacker comprised in said stacker unit either while a second handler that comprises gripper fingers for gripping said consumables transports said consumables from said intermediate station to at least one separation station for isolating nucleic acids or while said first handler transports consumables to at least one amplification station for amplifying nucleic acid, or while an analytical process is performed within said analyzer,
    unlocking said stacker unit when consumables are fully loaded into the stacker unit,
    closing said stacker unit, wherein said stacker unit is locked in its closed position to be operatively coupled to said transport system;
    wherein the steps of locking said stacker unit and unlocking said stacker unit are controlled by a computer controller.

12. The method of claim 11, wherein, when closing the stacker unit, the stacker unit automatically slides into a first end position within the analyzer.

13. The method of claim 12, wherein the sliding of the stacker unit between the first end position and a second end positions outside of the analyzer is fully automated.

14. The method of claim 13, further comprising as a first step:
    displaying on a display time windows for a user to load or unload consumables into the stacker unit.

15. The method of claim 12, further comprising as a first step:
    displaying on a display time windows for a user to load or unload consumables into the stacker unit.

16. The method of claim 11, further comprising as a first step:
    displaying on a display time windows for a user to load or unload consumables into the stacker unit.

17. The method of claim 11, wherein more than two different types of consumables are loaded into the analyzer wherein any one stacker is constructed and arranged to receive one specific type of consumables.

18. The method of claim 17, wherein each one type of said more than two different types of consumables comprises a unique surface geometry.

* * * * *